United States Patent
Zheng et al.

(10) Patent No.: US 11,618,871 B2
(45) Date of Patent: Apr. 4, 2023

(54) INTEGRATED TWO-PHASE ANAEROBIC DRY FERMENTATION REACTOR BASED ON BIOMIMETIC PRINCIPLE OF RUMEN

(71) Applicant: CHINESE RESEARCH ACADEMY OF ENVIRONMENTAL SCIENCES, Beijing (CN)

(72) Inventors: Mingxia Zheng, Beijing (CN); Jing Su, Beijing (CN); Beidou Xi, Beijing (CN); Xin Hao, Beijing (CN); Yuanyuan Sun, Beijing (CN); Mao Lin, Beijing (CN); Juan Li, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 606 days.

(21) Appl. No.: 16/632,352

(22) PCT Filed: May 18, 2018

(86) PCT No.: PCT/CN2018/087432
§ 371 (c)(1),
(2) Date: Jan. 19, 2020

(87) PCT Pub. No.: WO2019/148694
PCT Pub. Date: Aug. 8, 2019

(65) Prior Publication Data
US 2020/0208085 A1   Jul. 2, 2020

(30) Foreign Application Priority Data
Feb. 5, 2018 (CN) .......................... 201810111258.7

(51) Int. Cl.
C02F 11/04 (2006.01)
C12M 1/107 (2006.01)
(Continued)

(52) U.S. Cl.
CPC ............. *C12M 21/04* (2013.01); *C02F 11/04* (2013.01); *C12M 21/16* (2013.01); *C12M 23/26* (2013.01);
(Continued)

(58) Field of Classification Search
CPC ...... C12M 21/04; C12M 21/16; C12M 23/26; C12M 23/34; C12M 23/36; C12M 23/38;
(Continued)

(56) References Cited

U.S. PATENT DOCUMENTS 5,411,575 A * 5/1995 Fleming .................... C25C 1/12
75/743
2016/0376178 A1 * 12/2016 Xiang ..................... C02F 3/308
210/605

FOREIGN PATENT DOCUMENTS

CN  201071344 Y   6/2008
CN  102827761 A   12/2012
(Continued)

OTHER PUBLICATIONS

Machine-generated English translation of JP 2007-216135 A, dated Aug. 15, 2022.*
(Continued)

*Primary Examiner* — Fred Prince
(74) *Attorney, Agent, or Firm* — Bayramoglu Law Offices LLC

(57) ABSTRACT

An integrated two-phase anaerobic dry fermentation reactor based on a biomimetic principle of rumen includes a reactor body; wherein the reactor body includes a dry fermentation chamber, a secondary fermentation chamber, and a liquid storage chamber. The dry fermentation chamber is arranged at an upper portion of the reactor body. The liquid storage chamber is arranged at a bottom of the reactor body. The secondary fermentation chamber is arranged between the
(Continued)

dry fermentation chamber and the liquid storage chamber in the reactor body. The dry fermentation chamber is connected to the secondary fermentation chamber by a porous structure.

15 Claims, 1 Drawing Sheet

(51) Int. Cl.
C12M 1/16 (2006.01)
C12M 1/00 (2006.01)
C12M 1/06 (2006.01)
C12M 1/26 (2006.01)
C12M 1/02 (2006.01)
C12M 1/34 (2006.01)
C12P 5/02 (2006.01)

(52) U.S. Cl.
CPC ............ *C12M 23/34* (2013.01); *C12M 23/36* (2013.01); *C12M 23/38* (2013.01); *C12M 27/02* (2013.01); *C12M 29/06* (2013.01); *C12M 29/18* (2013.01); *C12M 33/14* (2013.01); *C12M 33/22* (2013.01); *C12M 41/12* (2013.01); *C12M 41/14* (2013.01); *C12M 41/18* (2013.01); *C12M 41/26* (2013.01); *C12P 5/023* (2013.01); *C02F 2209/02* (2013.01); *C02F 2209/06* (2013.01); *Y02E 50/30* (2013.01)

(58) Field of Classification Search
CPC ...... C12M 27/02; C12M 29/06; C12M 29/18; C12M 33/14; C12M 33/22; C12M 41/12; C12M 41/14; C12M 41/18; C12M 41/26; C02F 11/04; C02F 2209/02; C02F 2209/06; C12P 5/023; Y02E 50/30
USPC ........ 435/243, 289.1, 297.5, 300.1; 210/603, 210/612, 613, 614
See application file for complete search history.

(56) References Cited

FOREIGN PATENT DOCUMENTS

| | | | |
|---|---|---|---|
| CN | 203754471 U | 8/2014 | |
| CN | 203807355 U | 9/2014 | |
| CN | 104371915 A | 2/2015 | |
| CN | 204298395 U | 4/2015 | |
| CN | 204356326 U | 5/2015 | |
| CN | 106701544 A | 5/2017 | |
| CN | 206599566 U | 10/2017 | |
| CN | 206692642 U | 12/2017 | |
| WO | 0109280 A2 | 2/2001 | |

OTHER PUBLICATIONS

Machine-generated English translation of CN 107117718 A, dated Aug. 15, 2022.*
Machine-generated English translation of CN 205368348 U, dated Aug. 15, 2022.*

* cited by examiner

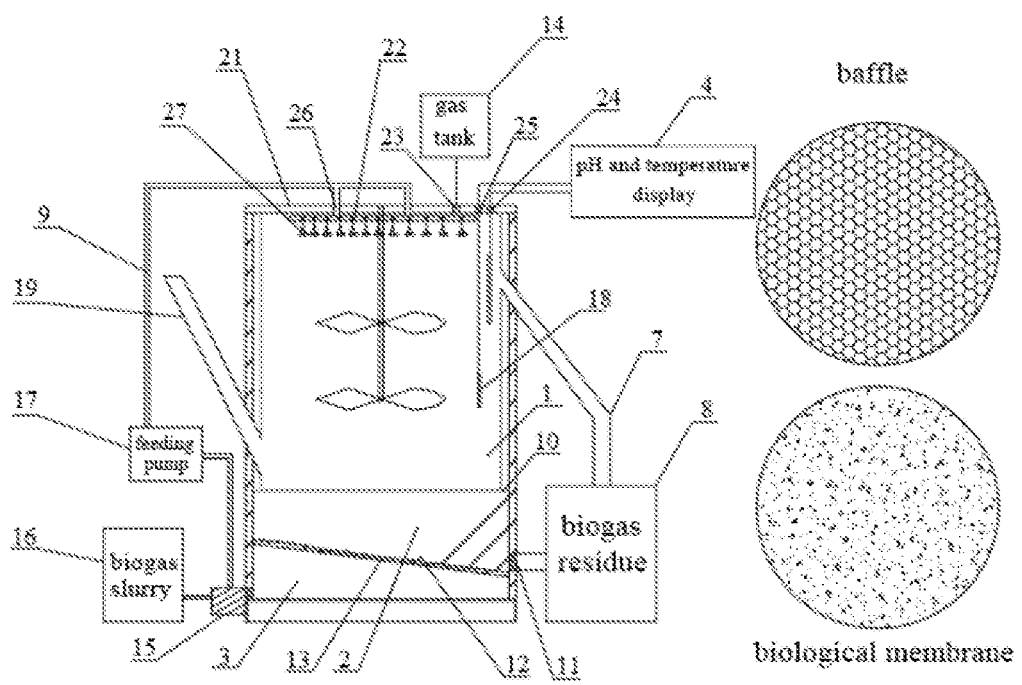

INTEGRATED TWO-PHASE ANAEROBIC DRY FERMENTATION REACTOR BASED ON BIOMIMETIC PRINCIPLE OF RUMEN

CROSS REFERENCE TO THE RELATED APPLICATIONS

This application is the national phase entry of International Application No. PCT/CN2018/087432, filed on May 18, 2018, which is based upon and claims priority to Chinese Patent Application No. 201810111258.7, filed on Feb. 5, 2018, the entire contents of which are incorporated herein by reference.

TECHNICAL FIELD

The present disclosure relates to the technical field of anaerobic fermentation of organic solid wastes, such as livestock feces, crop straws, kitchen wastes, dewatered sludge, and more. The present disclosure particularly relates to an integrated two-phase anaerobic dry fermentation reactor based on the biomimetic principle of rumen.

BACKGROUND

Organic anaerobic fermentation is a common microbial organic degradation technology, including both wet fermentation and dry fermentation. These types of fermentation are applied according to the dry matter content of the raw material. In general, the wet fermentation is applied to a case where the dry matter content is below 8%-12%. The dry fermentation refers to a process of producing biogas by the anaerobic fermentation of the raw material having a dry matter content of 20%-40%.

The anaerobic dry fermentation technology is an effective way to dispose of organic wastes, such as livestock feces, crop straws, kitchen wastes and dewatered sludge. Compared with the wet fermentation, the dry anaerobic fermentation has the advantages of less water consumption, modest secondary pollution, low energy consumption, and high energy efficiency. This technology has drawn a great deal of interest from researchers at home and abroad in recent years as it relates to specific waste materials, such as livestock dry feces, domestic wastes, urban dewatered sludge and straws. Since the waste materials water content is low, it is preferable to employ the dry fermentation technology.

In the dry fermentation technology, the dry matter content is high, resulting in a lack of fluidity and a poor condition of transferring heat and mass. The methanogenic microorganisms are particularly sensitive about the environmental factor and it is likely to bring about severe local acidification during the fermentation process. Moreover, ammonia inhibition readily arises when the livestock feces is used as a fermentation substrate, posing a sharp drop in biogas output.

In view of this, based on the biomimetic principle of rumen, the present disclosure provides an integrated two-phase anaerobic dry fermentation reactor to solve the existing problems in the dry fermentation technology of the prior art.

SUMMARY

The objective of the present disclosure is to provide an integrated two-phase anaerobic dry fermentation reactor based on the biomimetic principle of rumen, which has a high fermentation efficiency and has the capability to avoid acid inhibition and ammonia inhibition in the anaerobic dry fermentation of organic solid wastes, such as livestock feces, crop straws, kitchen wastes, and dewatered sludge.

In order to achieve the foregoing objective, the present disclosure employs the following technical solutions: an integrated two-phase anaerobic dry fermentation reactor based on the biomimetic principle of rumen, including; a reactor body, a gas collection device, a stirring system; a pH monitoring system; a temperature control system; a thermal insulation device; a biogas slurry storage tank; a biogas slurry backflow spraying device; and a biogas residue storage tank;

the reactor body includes a dry fermentation chamber, a secondary fermentation chamber, and a liquid storage chamber, wherein the dry fermentation chamber is arranged at an upper portion of the reactor body, a head cover on a top of the dry fermentation chamber is provided with a biogas outlet; a temperature measuring hole, a pH measuring hole and a plurality of biogas slurry inlets; a bottom of the dry fermentation chamber is a porous plate structure, and is covered with a flexible filter mesh with a hole size of not more than 2 mm; a side wall of a lower portion of the dry fermentation chamber is provided with a feed port, and a side wall of an upper portion of the dry fermentation chamber is provided with a discharge port; the liquid storage chamber is arranged at a bottom of the reactor body; a side wall of a bottom of the liquid storage chamber is provided with a biogas slurry outlet; the secondary fermentation chamber is arranged between the dry fermentation chamber and the liquid storage chamber in the reactor body; a bottom of the secondary fermentation chamber is provided with a porous plate having a tilted angle of not more than 15 degrees; the porous plate is covered with an ultrafiltration membrane; a biogas residue outlet is arranged on a side wall of the bottom of the secondary fermentation chamber; and a valve is arranged at the biogas residue outlet;

the gas collection device is connected to the dry fermentation chamber through the biogas outlet;

the stirring system includes a double-bladed stirrer and a motor, and is installed in a middle portion of the head cover of the reactor body for intermittent stirring;

the pH monitoring system is placed into the dry fermentation chamber through the head cover of the reactor body;

the temperature control system measures a temperature in the dry fermentation chamber through the temperature measuring hole, and the thermal insulation device adjusts the temperature in the dry fermentation chamber in real time through a feedback from the temperature control system;

the biogas slurry storage tank is connected to the biogas slurry outlet, and the biogas slurry backflow spraying device is connected to the biogas slurry storage tank through the biogas slurry inlet; the biogas residue storage tank is respectively connected to the discharge port at the side wall of the upper portion of the dry fermentation chamber and the biogas residue outlet at the side wall of the bottom of the secondary fermentation chamber;

the biogas slurry backflow spraying device includes a biogas slurry feeding pump, a biogas slurry pipeline and a spraying device, wherein the biogas slurry feeding pump is arranged outside the biogas slurry storage tank, an inlet of the biogas slurry feeding pump sprays biogas slurry into the dry fermentation chamber through the biogas slurry pipeline and the biogas slurry inlet; the spraying device includes a communication pipe and a plurality of nozzles, wherein one end of the communication pipe is connected to the biogas slurry pipeline, and the other ends are connected to the plurality of nozzles. Each nozzle sprays the biogas slurry into the dry fermentation chamber through the corresponding biogas slurry inlets.

On account of the foregoing technical solutions, the present disclosure has the following advantages: the present disclosure is provided with the reactor body, the gas collection device, the stirring system, the pH monitoring system, the temperature control system, the thermal insulation device, the biogas slurry storage tank, the biogas slurry backflow spraying device, and the biogas residue storage tank; the dry fermentation chamber, the secondary fermentation chamber and the liquid storage chamber are respectively arranged in the upper portion, the middle portion and the lower portion of the reactor body; the bottom of the dry fermentation chamber is provided with the flexible filter mesh with a hole size of not more than 2 mm; the side wall of the bottom of the dry fermentation chamber is provided with a feed port; the side wall of the top of the dry fermentation chamber is provided with a discharge port; the bottom of the secondary fermentation chamber is provided with a porous plate having a tilted angle of not more than 15 degrees; the porous plate is covered with an ultrafiltration membrane to filter the biogas slurry; the biogas slurry backflow spraying device is respectively connected to the dry fermentation chamber and the liquid storage tank through the biogas slurry outlet and the biogas slurry inlet. In the present disclosure, the dry fermentation chamber is used for dry fermentation. According to the biomimetic principle of rumen, that is the functions of filtering the digestive juice by the stomach wall and the rumination of rumen, a filter mesh is arranged at the bottom of the dry fermentation chamber to separate the reactor body into a solid phase producing acid in the dry fermentation chamber and a liquid phase producing methane in the secondary fermentation chamber. The fermentation broth produced by the dry fermentation chamber is filtered to the secondary fermentation chamber, and the fermentation broth and a part of small particulate matter that is not completely degraded proceed to the secondary wet fermentation in the secondary fermentation chamber to produce methane, thereby further improving the material degradation rate and the methane production. The biogas slurry is filtered by the ultrafiltration membrane and then flows back for spraying, and at this time, the filtrate is relatively clear and would not block the nozzle. Furthermore, the biogas slurry can almost be completely reused, and some biogas slurry that is not thoroughly reused, can also satisfy the discharge standard, thereby avoiding secondary pollution to the environment. The backflow liquid can promote the degradation of the materials in the dry fermentation chamber and the production of volatile organic acids, and accelerate the elution and diffusion of volatile fatty acids and ammonia nitrogen. The amount of the volatile fatty acid and the ammonia nitrogen eluted in the secondary fermentation chamber is controlled by controlling the amount of spray and the spraying times, thereby avoiding the acid inhibition and the ammonia nitrogen inhibition in the secondary fermentation, making the fermentation efficiency high. Based on the foregoing advantages, the present disclosure can be widely applied to the treatment of solid organic wastes with a high dry matter content, such as livestock feces, crop straws, kitchen wastes, and dewatered sludge.

BRIEF DESCRIPTION OF THE DRAWINGS

FIGURE shows a structural schematic diagram showing an integrated two-phase anaerobic dry fermentation reactor based on the biomimetic principle of rumen according to the present disclosure.

DETAILED DESCRIPTION OF THE EMBODIMENTS

The present disclosure will be specifically described hereinafter with reference to the drawings and the embodiments.

As shown in FIG. 1, the integrated two-phase anaerobic dry fermentation reactor based on the biomimetic principle of rumen, including: the reactor body, the gas collection device, the stirring system, the pH monitoring system, the temperature control system, the thermal insulation device, the biogas slurry storage tank, the biogas slurry backflow spraying device, and the biogas residue storage tank, wherein the reactor body includes the dry fermentation chamber 1, the secondary fermentation chamber 2, and the liquid storage chamber 3. The dry fermentation chamber 1 is arranged at the upper portion of the reactor body, the movable head cover 21 arranged on the top of the dry fermentation chamber is provided with the biogas outlet 23, the temperature measuring hole 24, the pH measuring hole 25 and the plurality of biogas slurry inlets 26. The bottom of the dry fermentation chamber is the porous plate structure 10 covered with the flexible filter mesh with a hole size of not more than 2 mm, allowing the fermentation broth and a part of the small particulate matter to enter the secondary fermentation chamber. A side wall of the lower portion of the dry fermentation chamber is provided with the feed port 19, and a side wall of the upper portion of the dry fermentation chamber is provided with the discharge port 7. The liquid storage chamber 3 is arranged at a bottom of the reactor body, and a side wall of a bottom of the liquid storage chamber is provided with the biogas slurry outlet 15. The secondary fermentation chamber 2 is arranged between the dry fermentation chamber 1 and the liquid storage chamber 3 in the reactor body. The fermentation broth and a part of the solid particles entering the secondary fermentation chamber are fermented again to produce methane, thereby enhancing the production rate of methane. The bottom of the secondary fermentation chamber 2 is provided with the porous plate 13 having a tilted angle of not more than 15 degrees. The porous plate is covered with the ultrafiltration membrane 12, and the biogas slurry is filtered through the ultrafiltration membrane and enters the liquid storage chamber 3. The biogas residue outlet 11 is arranged on a side wall of the bottom of the secondary fermentation chamber 2, and the porous plate 13 is designed to be inclined, which facilitates the biogas residue to slide into the biogas residue outlet 11 owing to gravity.

The gases generated in the dry fermentation chamber 1 and the secondary fermentation chamber 2 are collected and conveyed into the biogas storage tank 14 through the biogas outlet 23.

The biogas slurry backflow spraying device includes the biogas slurry feeding pump 17, the biogas slurry conveying pipeline 9 and the spraying device 22. The biogas slurry backflow spraying device is connected to the biogas slurry outlet 15 and the biogas slurry inlet 26 through the biogas slurry feeding pump 17. The biogas slurry outlet 15 is arranged between an outlet of the biogas slurry storage tank 16 and the biogas slurry feeding pump 17. The biogas slurry is conveyed into the spraying device of the biogas slurry inlet 26 through the biogas slurry conveying pipeline 9. The spraying device is formed by connecting the plurality of perforated pipelines 22 and the plurality of nozzles 27, and each of the plurality of nozzles 27 sprays the biogas slurry toward the dry fermentation chamber 1.

The pH monitoring system places the pH probe 18 into the dry fermentation chamber 1 through the pH measuring hole 25, and the pH value is read from the data display 4.

The temperature in the dry fermentation chamber 1 is measured by the temperature control system through the temperature measuring hole 24, and the temperature in the reactor body is adjusted by the thermal insulation device in real time according to the measured temperature.

The operating process of the integrated two-phase anaerobic dry fermentation reactor based on the rumen bionic concept includes two modes. One is a batching operation mode and the other is a semi-continuous operation mode. The batching operation mode is as follows. The pretreated raw material, the right amount of water and the right amount of inoculum are uniformly mixed at a time and are added into the dry fermentation chamber 1 through the feed port 19, and the solid content proportion of 20%-40% in the dry fermentation chamber 1 remains at 20%-40%. The raw material is fermented in the dry fermentation chamber 1 to produce a large amount of fermentation broth with volatile organic acids and a small amount of biogas a, and the fermentation broth enters the secondary fermentation chamber 2 through the porous plate and the flexible filter mesh at the bottom of the dry fermentation chamber 1. Meanwhile, the particulate matter passing through the filter mesh can also enter the secondary fermentation chamber 2 for secondary fermentation to generate a large amount of the biogas b. The biogas b moves up through the filter mesh at the bottom of the dry fermentation chamber 1, and enters the biogas storage tank 14 together with the biogas a through the biogas outlet 23. The biogas slurry in the secondary fermentation chamber 2 penetrates the inclined porous plate 13 of a solid-liquid separation device and the ultrafiltration membrane 12 covering on the porous plate 13 to enter the liquid storage chamber 3. When the biogas slurry in the liquid storage chamber 3 needs to be pumped out, the valve of the biogas slurry storage tank 16 is closed, and the biogas slurry feeding pump 17 pumps the biogas slurry to the nozzle of the spraying device 22 to spray the biogas slurry to the dry fermentation chamber 1, so as to adjust the solid content proportion in the dry fermentation chamber 1, and in a way function as stirring. When spraying is not required, the biogas slurry flows into the biogas slurry storage tank 16. The remaining filtered biogas residue in the secondary fermentation chamber 2, is deposited on the tilted porous plate 13, and gradually slides into the biogas residue outlet 11 owing to gravity, and enters the biogas residue storage tank 8. The biogas residue can be used as an organic fertilizer. After the reaction is completed, the residue in the dry fermentation chamber 1 and the secondary reaction chamber 2 is cleaned to the biogas residue storage tank 8 until commencement of the next batch of anaerobic fermentation.

The semi-continuous operation mode is as follows. The raw material, the water and the inoculum are placed into the dry fermentation chamber 1 according to a certain proportion, and the solid content proportion in the dry fermentation chamber 1 remains at 20%-40%. A predetermined amount of raw material is added into the feed port 19 everyday according to a set residence time and an organic load. Meanwhile, the valve of the discharge port 7 is opened, and the biogas residue is extruded out from the discharge port 7 into the biogas residue storage tank 8 by extrusion of the feedstock. The other operating processes are the same as the batch operation mode described above.

The structures and the connection manners of the components, the methods and the steps described above may be varied, any equivalent conversions and improvements made on the basis of the technical solutions of the present disclosure should not be excluded from the scope of protection of the present disclosure.

What is claimed is:

1. An integrated two-phase anaerobic dry fermentation reactor, comprising: a reactor body; wherein the reactor body comprises a dry fermentation chamber, a secondary fermentation chamber, and a liquid storage chamber, wherein the dry fermentation chamber is arranged at an upper portion of the reactor body; the liquid storage chamber is arranged at a bottom of the reactor body; the secondary fermentation chamber is arranged between the dry fermentation chamber and the liquid storage chamber in the reactor body; and a bottom of the dry fermentation chamber is connected to the secondary fermentation chamber by a porous structure.

2. The integrated two-phase anaerobic dry fermentation reactor according to claim 1, further comprising: a gas collection device, a stirring system, a pH monitoring system, a temperature control system, a thermal insulation device, a biogas slurry storage tank, a biogas slurry backflow spraying device, and a biogas residue storage tank.

3. The integrated two-phase anaerobic dry fermentation reactor according to claim 2, wherein the gas collection device is connected to the dry fermentation chamber through a biogas outlet; the stirring system is installed in a middle portion of a head cover of the reactor body; the pH monitoring system is placed into the dry fermentation chamber through the head cover of the reactor body; the temperature control system measures a temperature in the dry fermentation chamber through a temperature measuring hole, and the thermal insulation device adjusts the temperature in the dry fermentation chamber in real time through a feedback of the temperature control system; the biogas slurry storage tank is connected to a biogas slurry outlet; the biogas slurry backflow spraying device is connected to the biogas slurry storage tank through a biogas slurry inlet; the biogas residue storage tank is respectively connected to a discharge port at a side wall of an upper portion of the dry fermentation chamber and the biogas residue outlet at a side wall of a bottom of the secondary fermentation chamber; and the integrated two-phase anaerobic dry fermentation reactor is designed and operated based on a biomimetic principle of a rumen.

4. The integrated two-phase anaerobic dry fermentation reactor according to claim 3, wherein the porous structure is a porous plate structure, and the porous structure is covered with a flexible filter mesh with a hole size of not more than 2 mm.

5. The integrated two-phase anaerobic dry fermentation reactor according to claim 2, wherein the stirring system comprises a double-bladed stirrer and a motor; and the biogas slurry backflow spraying device comprises a biogas slurry feeding pump, a biogas slurry pipeline and a spraying device.

6. The integrated two-phase anaerobic dry fermentation reactor according to claim 2, wherein the porous structure is a porous plate structure, and the porous structure is covered with a flexible filter mesh with a hole size of not more than 2 mm.

7. The integrated two-phase anaerobic dry fermentation reactor according to claim 1, wherein a head cover arranged on a top of the dry fermentation chamber is provided with a biogas outlet, a temperature measuring hole, a pH measuring hole and a plurality of biogas slurry inlets; a side wall of a lower portion of the dry fermentation chamber is provided with a feed port, and a side wall of an upper portion of the dry fermentation chamber is provided with a discharge port; and a side wall of a bottom of the liquid storage chamber is provided with a biogas slurry outlet.

8. The integrated two-phase anaerobic dry fermentation reactor according to claim 7, wherein the porous structure is a porous plate structure, and the porous structure is covered with a flexible filter mesh with a hole size of not more than 2 mm.

9. The integrated two-phase anaerobic dry fermentation reactor according to claim 1, wherein a bottom of the secondary fermentation chamber is provided with a porous plate having a tilted angle.

10. The integrated two-phase anaerobic dry fermentation reactor according to claim 9, wherein the tilted angle of the porous plate is less than or equal to 15°.

11. The integrated two-phase anaerobic dry fermentation reactor according to claim 10, wherein the porous structure is a porous plate structure, and the porous structure is covered with a flexible filter mesh with a hole size of not more than 2 mm.

12. The integrated two-phase anaerobic dry fermentation reactor according to claim 9, wherein the porous plate is covered with an ultrafiltration membrane.

13. The integrated two-phase anaerobic dry fermentation reactor according to claim 12, wherein the porous structure is a porous plate structure, and the porous structure is covered with a flexible filter mesh with a hole size of not more than 2 mm.

14. The integrated two-phase anaerobic dry fermentation reactor according to claim 9, wherein the porous structure is a porous plate structure, and the porous structure is covered with a flexible filter mesh with a hole size of not more than 2 mm.

15. The integrated two-phase anaerobic dry fermentation reactor according to claim 1, wherein the porous structure is a porous plate structure, and the porous structure is covered with a flexible filter mesh with a hole size of not more than 2 mm.

* * * * *